United States Patent
Astorga-Wells (10) Patent No.: US 7,902,500 B2
(45) Date of Patent: Mar. 8, 2011

(54) METHODS AND INTERFACES FOR SINGLE AND MULTIDIMENSIONAL SEPARATIONS FOR CHARACTERIZATION AND/OR IDENTIFICATION OF MOLECULES BY MASS SPECTROMETRY

(75) Inventor: Juan Astorga-Wells, Skarpnack (SE)

(73) Assignee: PerkinElmer Health Sciences, Inc., Waltham, MA (US)

( * ) Notice: Subject to any disclaimer, the term of this patent is extended or adjusted under 35 U.S.C. 154(b) by 596 days.

(21) Appl. No.: 11/792,689

(22) PCT Filed: Dec. 6, 2005

(86) PCT No.: PCT/SE2005/001844
§ 371 (c)(1),
(2), (4) Date: Jun. 6, 2007

(87) PCT Pub. No.: WO2006/062471
PCT Pub. Date: Jun. 15, 2006

(65) Prior Publication Data
US 2007/0267573 A1 Nov. 22, 2007

(30) Foreign Application Priority Data
Dec. 6, 2004 (SE) ...................... 0402966

(51) Int. Cl.
*H01J 49/04* (2006.01)
(52) U.S. Cl. ........ 250/288; 250/281; 250/282; 204/450; 204/451; 204/542; 204/545
(58) Field of Classification Search .................. 250/281, 250/282, 288; 204/450, 451, 542, 545
See application file for complete search history.

(56) References Cited

U.S. PATENT DOCUMENTS 5,505,832 A * 4/1996 Laukien et al. ............... 204/452
(Continued)

FOREIGN PATENT DOCUMENTS

WO WO 2004/056697 7/2004

OTHER PUBLICATIONS

"A Microfluidic Electrocapture Device in Sample Preparation for Protein Analysis by MALDI Mass Spectrometry", Astorga-Wells et al., Analytical Chemistry 2003, vol. 75, pp. 5213-5219, available online Oct. 15, 2003.*

(Continued)

*Primary Examiner* — Robert Kim
*Assistant Examiner* — Nicole Ippolito Rausch
(74) *Attorney, Agent, or Firm* — Fish & Richardson P.C.

(57) ABSTRACT

The present invention relates a use of the electrocapture-based separation technology combined with mass spectrometry (e.g. sequence of polypeptides by collision-induce dissociation mass spectrometry, for the identification and/or characterization molecules of interest). In addition, it relates physical interfaces between electrocapture-based separations and different types mass spectrometers for on-line analysis, as well as the coupling of electrocapture-based separations, liquid chromatography and different types of mass spectrometrometers. It also relates the combination of the electrocapture-base separation technology with other liquid separation methods, as e.g. liquid chromatography, in order to achieve multidimensional separations prior mass spectrometrical analysis. The invention also relates to a separation device comprising a capture device, a fluidic connector e.g. an electrospray source, an electrospray interface-source and a mass spectrometer.

33 Claims, 4 Drawing Sheets

U.S. PATENT DOCUMENTS

| | | | |
|---|---|---|---|
| 6,396,057 | B1 | 5/2002 | Jarrell et al. |
| 6,831,271 | B1 | 12/2004 | Guevremont et al. |
| 2003/0150987 | A1 | 8/2003 | Guevremont et al. |
| 2003/0201390 | A1 | 10/2003 | Corso et al. |
| 2004/0041093 | A1* | 3/2004 | Schultz et al. ............... 250/288 |
| 2004/0072337 | A1 | 4/2004 | Moon et al. |
| 2005/0284762 | A1* | 12/2005 | Astorga-Wells et al. ..... 204/451 |
| 2006/0145071 | A1* | 7/2006 | Frazer et al. ................. 250/288 |
| 2006/0263904 | A1* | 11/2006 | Morozov et al. .............. 436/518 |

OTHER PUBLICATIONS

Buryakov, et al., "A new method of separation of multiatomic fans by mobility at atmospheric pressure using a high-frequency amplitude-asymmetric strong electric field," Int. J. of Mass Spectrometry and Ion Processes, 128(3):143-148, (1993).

Astorga-Wells, "Microfluidic Electrocapture Technology in Protein and Peptide Analysis," Thesis: From the Department of Medical Biochemistry and Biophysics Karolinska Institute, Stockholm, Sweden, 2004.

Supplementary European search report for corresponding EP Application No. 05813450.3, dated Oct. 21, 2010.

* cited by examiner

METHODS AND INTERFACES FOR SINGLE AND MULTIDIMENSIONAL SEPARATIONS FOR CHARACTERIZATION AND/OR IDENTIFICATION OF MOLECULES BY MASS SPECTROMETRY

CROSS-REFERENCE TO RELATED APPLICATIONS

This application claims the priority of International Application PCT/SE05/01844, filed Dec. 6, 2005. PCT/SE05/01844 claims the priority of SE 0402966-6, filed on Dec. 6, 2004.

DESCRIPTION

BACKGROUND

The present invention represents a novel mode to utilize a device described in PCT/SE2003/002027, which has been published as WO 2004/056697, the entire contents of which are incorporated herein by reference. The key innovative steps in this invention are:

Methods and interfaces for the combination of electrocapture-based separations (described in PCT/SE2003/002027, WO 2004/056697) with mass spectrometry for characterization and/or identification of molecules of interest. Mass spectrometry (MS) is a powerful analytical tool for the identification and characterization of peptides, proteins, DNA, RNA, drugs, other polymers and small molecules. Even though MS can analyze samples containing more that one particular type of molecules, a separation step is usually necessary when analyzing a sample having a complex mixture of molecules. This is particularly true for samples derived from biological sources such as for example, blood, urine, saliva, cell extracts or fractions, bacteria extracts or fractions. Another important application where a separation step is necessary before MS analysis is in the identification of proteins via the enzyme digestion (e.g., trysin digestion) of a single protein (or a mixture of proteins) and the following separation and injection into the mass spectrometer. In this case peptides are separated and injected into the mass spectrometer, in which one peptide with a particular mass and charge ratio (m/z) is selected for fragmentation followed by tandem mass spectrometry (MS/MS). Utilizing MS/MS, the m/z value of the fragments are determined, thus making the determination of the amino acid sequence of the particular peptide possible, in order to identify the protein from which the peptide was derived (via database search). For all these mixtures of molecules, the separation step improves the performance of the overall analysis by mass spectrometry (higher number of molecules are characterized and/or identified with increased sensitivity).

SUMMARY

The connection of the electrocapture based separation with mass spectrometry is not a trivial issue, since molecules need to be both ionized and in the gas-phase in order to be injected into the mass spectrometer.

The separation with the electrocapture device must be performed in solution (molecules are dissolved in a particular solvent), thus a particular interface and method should be developed to combine this two techniques.

In addition, another critical issue is that the interface (or connection) between both technologies must be done without disrupting the separation process.

One of the innovative steps described in this application is to combine electospray ionization mass spectrometry (ESI-MS) with the electrocapture device to separate molecules of interest. In electrospray ionization, molecules are ionized and transferred to the gas-phase by applying an electric field (about 1000 and 3000 kV) between the solution, where the molecules of interest are dissolved, and the mass spectrometer. Not all aspects of electrospray ionization are fully understood, but it is known that electrostatic-repulsion and solvent characteristics (evaporation, surface tension and pH) play an important role. In brief, the difference of electric potential between the solution and the mass spectrometer induces the formation of the electrospray, which involves the formation of micrometer and nanometer size droplets (due to an electrostatic effect) that have the same charge. The latter causes the droplets to be repelled from one another (due to charge-to-charge repulsion). In parallel to this process, the solvent of the droplets starts to evaporate, and together with electrostatic repulsion, allow the molecules to be transferred to the gas-phase in an ionized state.

It is clear from the above that the electric potential between the solvent and the mass spectrometer must be applied during the electrospray ionisation-mass spectrometry (ESI-MS) analysis. It is here where problems arise from the connection of the capture device with ESI-MS. The capture device has at least two electrodes by which the molecules are captured and separated. For this reason, the voltage from the ESI must not interfere with the voltage in the capture device (and vice-versa). Therefore, if a proper voltage decoupling is not achieved, the electrospray process and/or the operation of the capture device will deteriorate to the extent that molecules are not separated/captured on the capture device and/or the electrospray process is not completed.

The decoupling is achieved by the use of a capillary having micrometer-sized dimensions (between 5 to 150 μm), and/or the use of buffers of low conductivity (using solutions of low salt concentration (e.g. between 1-20 mM and/or the use of solutions with organic solvents (e.g., acetonitrile, methanol) in a concentration between 99% to 1%) and/or the utilization of a capture device circuit voltage where the power supply of the capture device is electrically floating and thus does not interfere with the electrospray voltage. In addition, the decoupling can be achieved by using a sheath flow interface in which the electrospray voltage is applied to the electrospray solvent that travels coaxially to the outlet of the device, and is helped by a further coaxial flow of gas (sheath flow interfaces are generally known in the art and are for example described in the literature (e.g., Electrophoresis 2004, 25, 1927-1948)).

Another innovative step is the combination of electrocapture-based separations and chromatography separations with mass spectrometry. In addition to the connection of the eletrocapture device with electrospray ionization mass spectrometry, a step to further separate the molecules is to combine the electrocapture-based separation with a chromatography process (e.g., reverse phase chromatography) in order to carry out multidimensional separations. In this manner, the separation power of the electrocapture-based separations can be increased, resulting in an improvement of the performance of the MS measurements (higher number of molecules characterized and/or identified with increased sensitivity). The most common manner to perform multidimensional separation prior to mass spectrometry is by combining ion-exchange chromatography (where the separation is based on charge) with reverse-phase chromatography (where the separation is based on hydrophobicity). The main problem with this approach is that the ion-exchange chromatography needs salts to separate the molecules of interest. Salts can be detrimental to the mass spectrometer. Thus ion-exchange chromatography and reverse-phase chromatography can not be connected online, hindering the automation of the overall separation procedure. The electrocapture-based separations is a method that separates molecules according to electrophoretic mobility and does not use salts, making a straightforward connection to reverse-phase chromatography for multidimensional separation prior to mass spectrometry possible.

DETAILED DESCRIPTION

Figure 1:
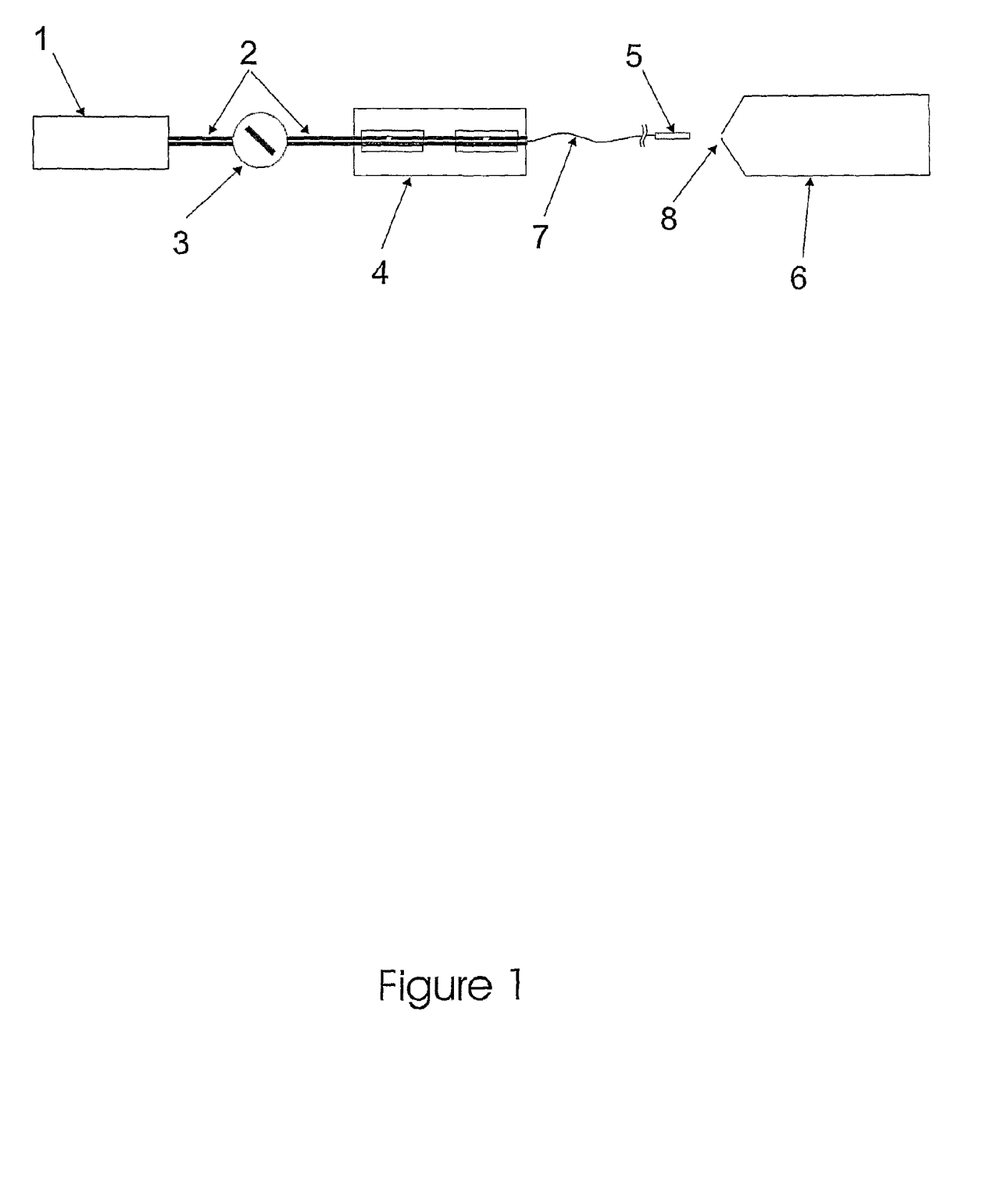
FIG. 1 shows an embodiment of a mass spectrometer integrated with an electrocapture device.

FIG. 1 shows an embodiment according to the invention. Reference FIG. 1 denotes a pump, 2 denotes fluidic connectors (pump injector-capture device), 3 denotes an injector, 4 denotes a capture device, 5 denotes an electrospray interface-source, 6 denotes a mass spectrometer, 7 denotes a fluidic connector (capture device-electrospray source) and 8 denotes the inlet of the mass spectrometer.

Figure 2:
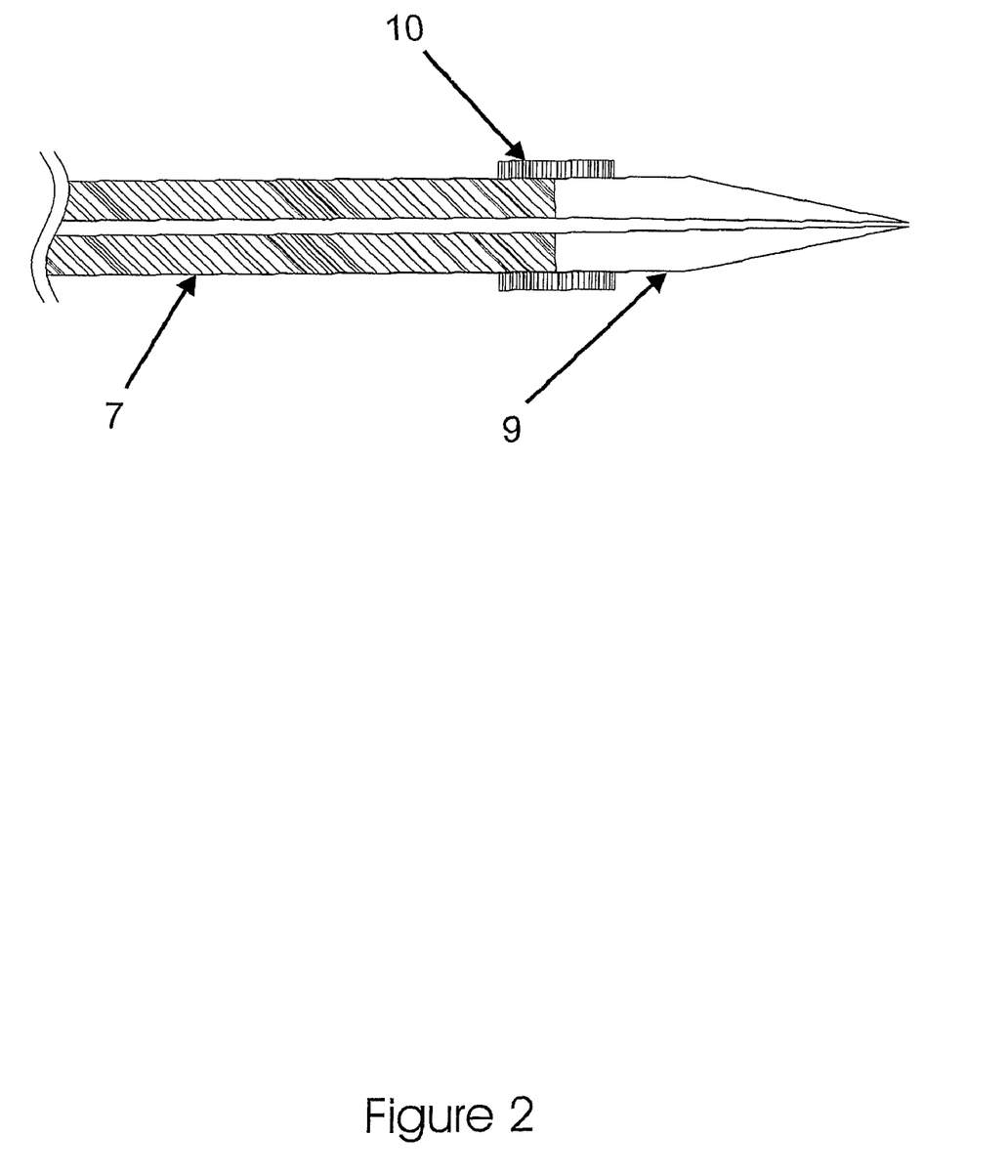
FIG. 2 shows an embodiment of the electrospray interface-source.

FIG. 2 shows details of the electrospray interface-source 5 of FIG. 1 wherein 9 is a tip coated with a conductive material and 10 is a connector with zero or low dead volume.

Figure 3:
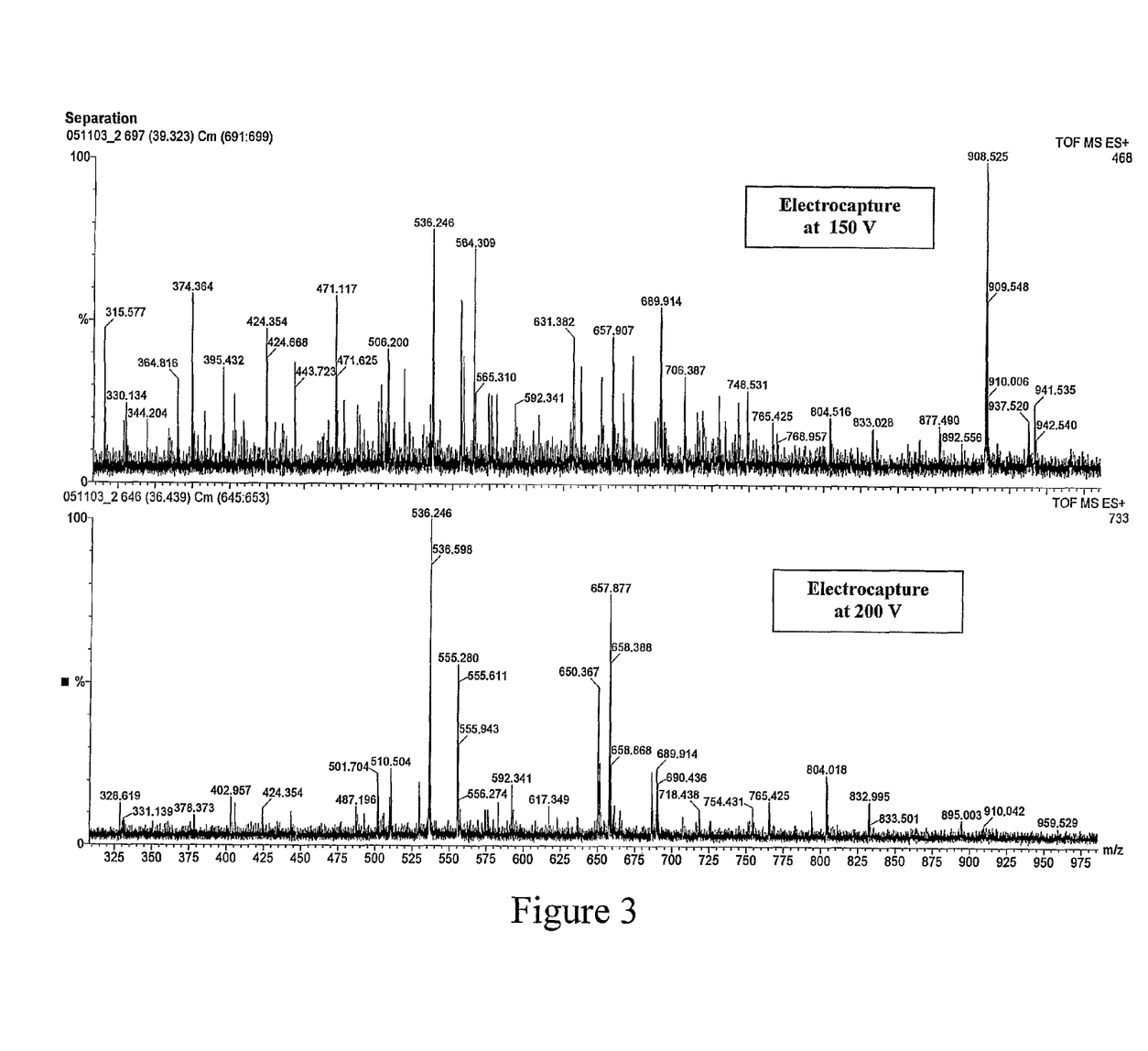
FIG. 3 shows ESI-mass spectra obtained when electrocapture-based separation is used.

FIG. 3. shows on-line electrocapture-based separations and ESI-Mass Spectra. The system setup includes a 1 µL-injector, a syringe pump, a power supply, an electrocapture device and a 50 µm fused silica capillary (20 cm) that connects the outlet of the electrocapture device to the electrospray source. The source is a silica capillary coated with a conductive material (for reference, see FIGS. 1 and 2), and the mass spectrometer is a Q-T of flight mass spectrometer. Peptides obtained from trypsin the digestion of 4 proteins (BSA, myoglobin, ADH and cytochrome C) dissolved in 10 mM $NH_4HCOO$ (pH 5,5 and 20% acetonitrile) are captured using an initial voltage drop of 300 V and a flow rate of 0.2 µL/min. As seen in the figure above, different peak profiles can be seen in the ESI-MS spectra by using different electrocapture voltages (200 and 250 V), showing that the electrocapture device can be coupled online to ESI-MS to fractionate molecules of interest.

Figure 4A:
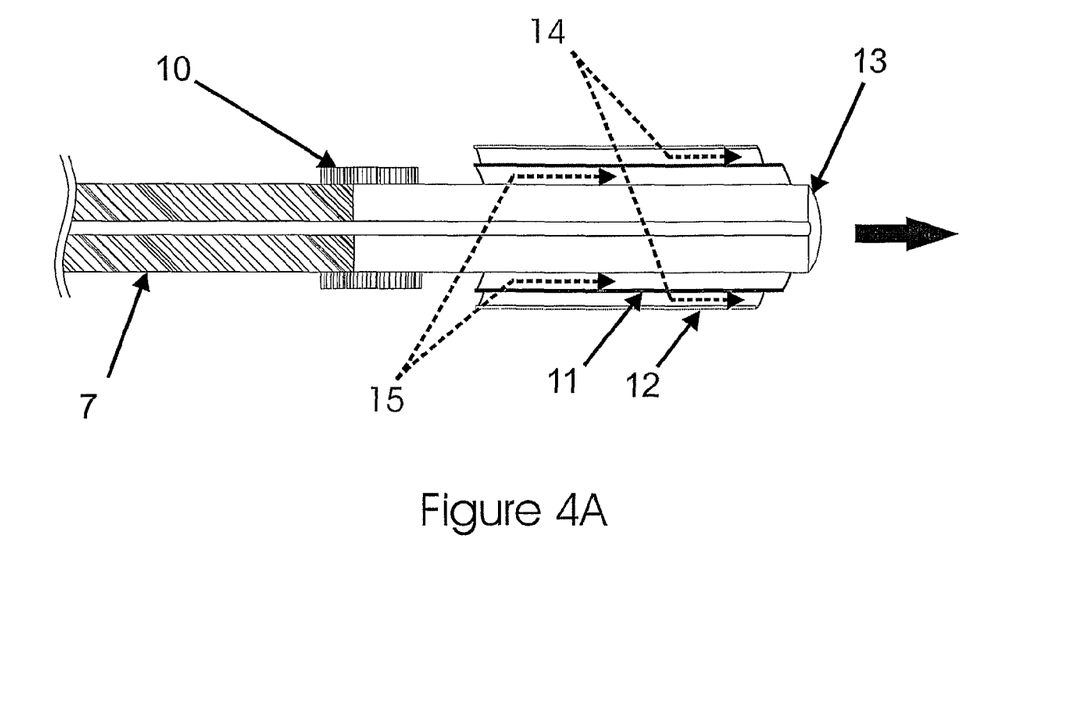
FIG. 4 shows an embodiment of the sheath flow interface.
Figure 4B:
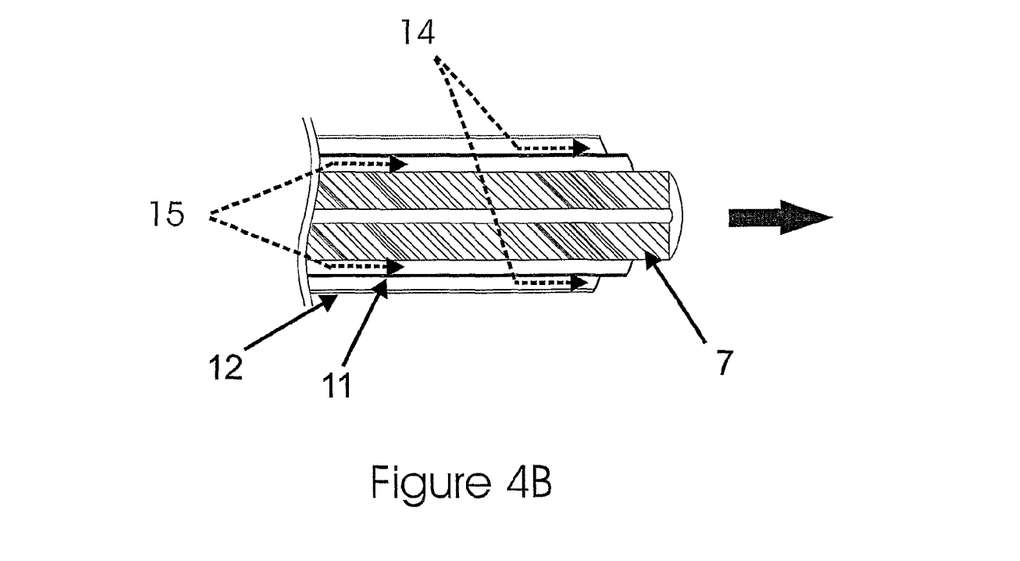

FIG. 4. shows a sheath flow interface for the connection of the electrocapture device with an electrospray ionization mass spectrometer. The figure shows two different embodiments of the interface (A and B). The sheath flow interfaces allow decoupling between the electrocapture device and electrospray voltages. In FIG. 4A the item 11 depicts an electrically conductive tube from which the electric field for the electrospray process is applied. An electrolyte solution is continuously flowing (pumped) in conductive tube 11. Item 12 depicts a tube in which a gas is continuously flown through. The gas (sheath gas, item 14) and the electrolyte (sheath liquid, item 15) are travelling coaxial to a capillary tube (13) preferably made of silica and connected to fluidic connector (7). FIG. 4B depicts another setup to decouple the voltages, here, the item 11 depicts an electrically conductive tube from which the electric field for the electrospray process is applied. In conductive tube (11) an electrolyte solution is continuously flowing (pumped). Item 12 depicts a tube where a gas is continuously flown through. The gas and the electrolyte are travelling coaxial to the fluidic connector (7). The arrow shows the direction to a mass spectrometer.

The invention also relates to a separation device featuring a capture device, a fluidic connector e.g., an electrospray source, an electrospray interface-source and a mass spectrometer. The electrospray interface-source may be a conductively coated tip connected to at least one connector. The conductive layer is made of any electrically conductive material such as a metal e.g., silver or gold. One or more chromatograhic columns capable of separating molecules by size or hydrophobicity could placed before or after the electrocapture device.

All specifications regarding materials and performance apply mutatis mutandis to both the methods and the devices according to the invention.

The invention claimed is:

1. An apparatus for analyzing molecules comprising:
 (a) an electrocapture device comprising at least two electrodes,
 (b) an electrospray source comprising a tip,
 (c) a mass spectrometer,
 (d) means to apply voltages to said electrodes,
 (e) means to apply an electric field between said electrospray source and said mass spectrometer, and
 (f) an interface connecting said electrocapture device and said electrospray source, wherein the interface comprises a sheath-flow interface.

2. The apparatus according to claim 1, whereby wherein said interface comprises a capillary tube.

3. The apparatus according to claims 2, wherein said capillary tube is a small bore capillary tube.

4. The apparatus according to claims 2, wherein said capillary tube is a fused silica capillary tube.

5. The apparatus according to claims 1, wherein said interface comprises a capillary tube having an entrance end and an exit end, said entrance end being connected to said electrocapture device and said exit end being connected to said electrospray source.

6. The apparatus according to claims 5, wherein said capillary tube is a fused silica capillary tube.

7. The apparatus according to claims 1, wherein said interface comprises a capillary tube connected to a tip, said tip being coated with an electrically conductive material.

8. The apparatus according to claim 7, wherein said capillary tube being connected at an end of said capillary to said tip with a zero or low dead volume connection.

9. The apparatus according to claim 7, wherein said sheath flow interface comprises a liquid sheath layer and a gas sheath layer flowing coaxially along said tip with said tip connected to said capillary tube.

10. The apparatus according to claims 1, wherein said interface comprises a tip is coated with an electrically conductive material.

11. The apparatus according to claims 1, wherein said interface comprises a capillary tube and said sheath flow interface comprises a liquid sheath layer and a gas sheath layer flowing coaxially along said capillary tube.

12. The apparatus according to claim 1, wherein said means to apply voltages to said electrodes comprises a power supply.

13. The apparatus according to claim 12, wherein said power supply of said electrocapture device is electrically floating.

14. The apparatus according to claim 1, wherein said mass spectrometer comprises means to conduct mass to charge analysis of ions produced in said electrospray source.

15. The apparatus according to claim 1, wherein said mass spectrometer comprises means to conduct MS/MS analysis of ions produced in said electrospray source.

16. The apparatus according to claim 1, wherein said apparatus comprises a liquid chromatogram configured after said electrocapture device.

17. The apparatus according to claim 1, wherein said apparatus comprises a liquid chromatogram configured before said electrocapture device.

18. A method for analyzing molecules comprising:
(a) utilizing an apparatus comprising an electrocapture device with at least two electrodes, an electrospray source comprising a tip, a mass spectrometer, means to apply voltages to said electrodes and means to apply an electric field between said electrospray source and said mass spectrometer and an interface connecting said electrocapture device and said electrospray source,
(b) conducting electrocapture of said molecules in solution in said electrocapture device and releasing of said molecules from said electrocapture device,
(c) electrospraying said molecules released from said electrocapture device forming gas phase ionized molecules, and
(d) analyzing said ionized molecules using said mass spectrometer,
wherein said interface comprises a capillary and conducting electrocapture and electrospraying of said molecules comprises co-axially flowing a liquid and a gas along said capillary.

19. The method according to claim 18, wherein said electrocaptured molecules are separated during said releasing of said molecules from said electrocapture device.

20. The method according to claim 19, wherein said molecules are electrocaptured and separated using said electrocapture device with on line electrospray ionization of separated molecules released from said electrocapture device.

21. The method according to claim 19 or 20, wherein said separated molecules are mass to charge analyzed using said mass spectrometer.

22. The method according to claim 19 or 20 wherein said separated molecules are MS/MS analyzed using said mass spectrometer.

23. The method according to claim 18 wherein one or more liquid chromatography columns is configured after said electrocapture device and said molecules released from said electrocapture device are further separated in said one or more liquid chromatography columns.

24. The method according to claim 23 wherein two dimensional separation of said chemical species is conducted using said electrocapture device and said liquid chromatography column on line with electrospray MS and/or MS/MS analysis.

25. The method according to claim 23, wherein said liquid chromatography columns are configured before and after said electrocapture device and multidimensional separation of chemical species is conducted using said liquid chromatography columns and said electrocapture device on line with electrospray MS and/or MS/MS analysis.

26. The method according to claim 25, wherein said multidimensional separation is performed by first separating molecules in said liquid chromatography column and second by separating molecules in said electrocapture device on line with electrospray MS and/or MS/MS analysis.

27. The method according to claim 18, wherein a liquid chromatography column is configured before said electrocapture device.

28. The method according to claim 18, wherein said electrocapture of molecules is performed using buffers of low conductivity and/or using solutions with organic solvents.

29. The method according to claim 28, wherein said low conductivity buffers comprise between 1 to 20 millimolar salt concentration and/or said organic solvent concentration comprises between 1% and 99% in water.

30. The method according to claim 18, wherein said electrospray is performed using sheath liquid and gas flow.

31. The method according to claim 18, wherein said electrospray is performed by spraying from a tip coated with an electrically conductive material.

32. The method of claim 18, wherein during electrospraying of said molecules voltages are applied to said electrodes is decoupled from the electric field between said electrospray source and said mass spectrometer.

33. The method according to claim 32, wherein said decoupling is achieved by applying said voltages to said electrodes using an electrically floating power supply.

* * * * *

UNITED STATES PATENT AND TRADEMARK OFFICE
CERTIFICATE OF CORRECTION

PATENT NO.        : 7,902,500 B2                         Page 1 of 2
APPLICATION NO.   : 11/792689
DATED             : March 8, 2011
INVENTOR(S)       : Juan Astorga-Wells It is certified that error appears in the above-identified patent and that said Letters Patent is hereby corrected as shown below:

Title Page, Col. 2, item (57); lines 9-10,
(Abstract), Delete "spectrometrometers." and insert --spectrometers.--

Column 4,
Line 29, after "1", delete "whereby"

Column 4,
Line 31, Delete "claims" and insert --claim--

Column 4,
Line 33, Delete "claims" and insert --claim--

Column 4,
Line 35, Delete "claims" and insert --claim--

Column 4,
Line 40, Delete "claims" and insert --claim--

Column 4,
Line 42, Delete "claims" and insert --claim--

Column 4,
Line 52, Delete "claims" and insert --claim--

Column 4,
Line 55, Delete "claims" and insert --claim--

Column 5,
Line 41, After "20" insert --,--

Signed and Sealed this
Thirtieth Day of August, 2011

David J. Kappos
*Director of the United States Patent and Trademark Office*

CERTIFICATE OF CORRECTION (continued)
U.S. Pat. No. 7,902,500 B2

<u>Column 6,</u>
Line 1, After "18" insert --,--

<u>Column 6,</u>
Line 6, After "23" insert --,--